(12) United States Patent
Terashima et al.

(10) Patent No.: US 6,797,832 B1
(45) Date of Patent: Sep. 28, 2004

(54) PROCESS FOR THE PRODUCTION OF 5-OXY-7-OXABICYCLO [4.1.0] HEPT-3-ENE-3-CARBOXYLIC ACID ESTERS

(75) Inventors: Shiro Terashima, Tokyo (JP); Katsuji Ujita, Kurashiki (JP); Tomoya Kuwayama, Kurashiki (JP); Takashi Sugioka, Kurashiki (JP); Kazuya Shimizu, Kurashiki (JP); Koichi Kanehira, Niigata (JP)

(73) Assignees: Sagami Chemical Research Center, Ayase (JP); Kuraray Co., Ltd., Kurashiki (JP)

( * ) Notice: Subject to any disclaimer, the term of this patent is extended or adjusted under 35 U.S.C. 154(b) by 13 days.

(21) Appl. No.: 10/168,388

(22) PCT Filed: Nov. 27, 2000

(86) PCT No.: PCT/JP00/08348

§ 371 (c)(1),
(2), (4) Date: Jun. 21, 2002

(87) PCT Pub. No.: WO01/47906

PCT Pub. Date: Jul. 5, 2001

(30) Foreign Application Priority Data

Dec. 27, 1999 (JP) ............................................. 11-371400

(51) Int. Cl.[7] .................... C07D 307/93; C07D 307/00; C07D 301/02; C07D 303/00
(52) U.S. Cl. ......................... 549/459; 549/545; 549/546
(58) Field of Search ................................ 549/459, 545, 549/546

(56) References Cited

U.S. PATENT DOCUMENTS

| 5,763,483 A | 6/1998 | Bischofberger et al. ..... 514/529 |
| 5,834,618 A | 11/1998 | Terashima et al. .......... 558/408 |

FOREIGN PATENT DOCUMENTS

| WO | 96/26933 | 9/1996 |
| WO | WO 98/07685 | 2/1998 |

OTHER PUBLICATIONS

Kunstmann et al, J. Am. Chem. Soc., vol. 84, pp. 4115–4125, 1962.*
S. Pornpakakul, et al., Tetrahedron Letters, vol. 41, pp. 2691–2694, XP–002240491, "Asymmetric Synthesis of (–)–4–epi–Shikimic Acid", 2000.
G. Mehta, et al., Tetrahedron Letters, vol. 39, No. 20, pp. 3285–3286, XP–004116253, "Norbornyl Route to Polyoxgenated Cyclohexanes. A Facile Entry into Carbasugars and Shikimic Acid", 1998.

(List continued on next page.)

*Primary Examiner*—Ba K. Trinh
(74) *Attorney, Agent, or Firm*—Oblon, Spivak, McClelland, Maier & Neustadt, P.C.

(57) ABSTRACT

The present invention provides a method of producing 5-oxy-7-oxabicyclo[4.1.0]hept-3-ene-3-carboxylic acid ester economically, industrially advantageously and efficiently in a large amount. The present invention is a method of producing 5-oxy-7-oxabicyclo[4.1.0]hept-3-ene-3-carboxylic acid ester (X), which is shown in the following scheme.

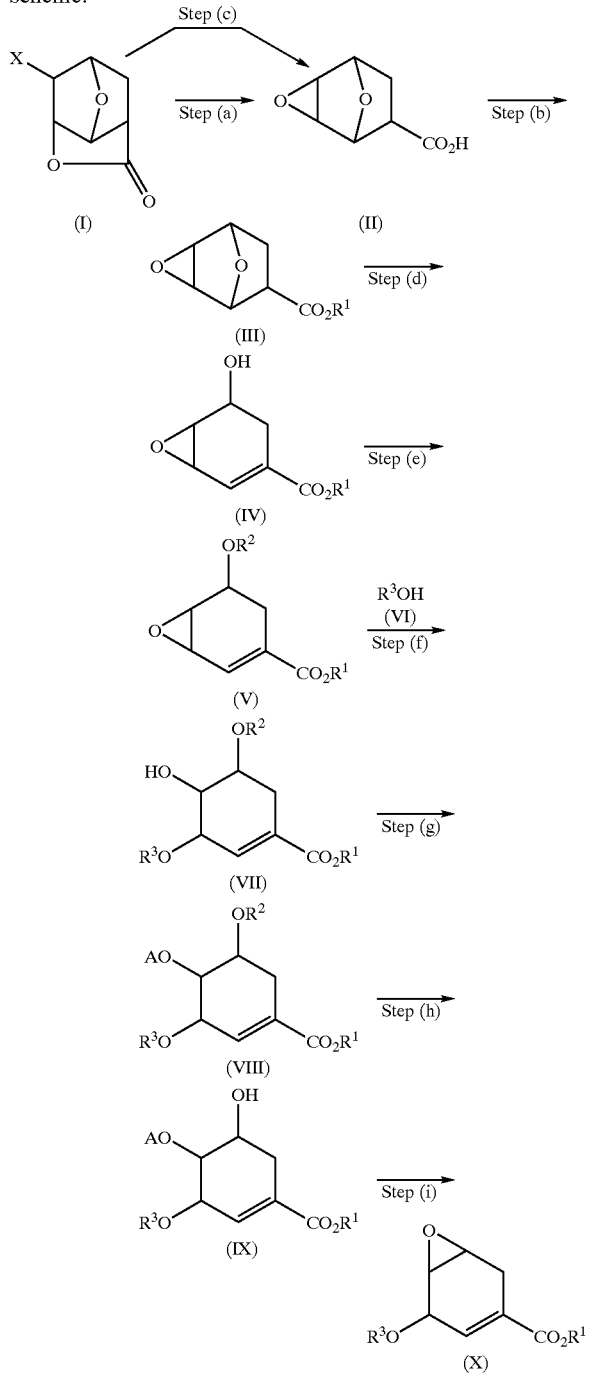

wherein each symbol is as defined in the specification.

10 Claims, No Drawings

OTHER PUBLICATIONS

H. Liu, et al., Bioorganic and Medicinal Chemistry Letter, vol. 7, No. 11, pp. 1419–1420, "Synthesis and Evaluation of 3–Deoxy–D–Manno–2–Octulosonate–8–Phosphate (KDO8P) Synthase Inhibitors", 1997.

J. C. Rohloff, et al., J. Org. Chem., vol. 63, No. 13, XP–002230661, pp. 4545–4550, "Practical Total Synthesis of the Anti–Influenza Drug GS–4101", 1998.

M. Federspiel, et al., Organic Process Research & Development, vol. 3, No. 4, XP–002230662, pp. 266–274, "Industrial Synthesis of the Key Precursor in the Synthesis of the Anti–Influenza Drug Oseltamivir Phosphate (Ro 64–0796/002, GS–4104–02): Ethyl (3R,4S,5S)–4,5–Epoxy–3(1–Ethyl–Propoxy)–Cyclohex–1–ene–1–Carboxylate", 1999.

H. Blair, et al., J. Am. Chem. Soc., vol. 112, No. 24, XP–002230663, pp. 8907–8909, "Short Chemical Synthesis of (–)–Chorismic Acid From (–)–Shikimic Acid", 1990.

D. Rajapaksa, et al., Can. J. Chem., vol. 62, XP–009005581, pp. 826–827, "Shikimic Acids From Furan: Methods of Stereocontrollled Access To 3,4,5–Trioxygenated Cyclohexenes", 1984.

G.P. Moss et al.: "Further rearrangements of diepoxycyclohexanes: formation of acetyldihydroxycyclopentane derivatives" Tetrahedron Lett., vol. 37, No. 16, pp. 2877–2880, 1996.

* cited by examiner

PROCESS FOR THE PRODUCTION OF 5-OXY-7-OXABICYCLO [4.1.0] HEPT-3-ENE-3-CARBOXYLIC ACID ESTERS

CROSS-REFERENCE TO RELATED APPLICATIONS

This application is a 371 Application of PCT/JP00/08348 filed Nov. 27, 2000.

TECHNICAL FIELD

The present invention relates to a production method of 5-oxy-7-oxabicyclo[4.1.0]hept-3-ene-3-carboxylic acid ester. 5-Oxy-7-oxabicyclo[4.1.0]hept-3-ene-3-carboxylic acid ester, such as ethyl (1β,5α,6β)-5-(1-ethylpropoxy)-7-oxabicyclo[4.1.0]hept-3-ene-3-carboxylate, obtained by the present invention, is useful as a synthetic intermediate for GS4104 represented by the following formula.

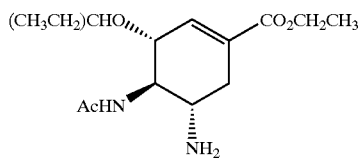

GS4104 is a compound under development as a novel agent for the prophylaxis or treatment of influenza based on its action to prevent viral growth by inhibiting neuraminidase present on the surface of influenza virus (hereinafter to be generally referred to as an anti-influenza drug) [see The Journal of Organic Chemistry (J. Org. Chem.), vol. 63, p. 4545 (1998); organic Process Research & Development, vol. 3, p. 266 (1999)].

BACKGROUND ART

As a conventional synthetic method of 5-oxy-7-oxabicyclo[4.1.0]hept-3-ene-3-carboxylic acid ester, such as ethyl (1β,5α,6β)-5-(1-ethylpropoxy)-7-oxabicyclo[4.1.0]hept-3-ene-3-carboxylate, a synthetic method wherein shikimic acid is used as a starting material [see The Journal of Organic Chemistry (J. Org. Chem.), vol. 63, p. 4545 (1998); Organic Process Research & Development, vol. 3, p. 266 (1999); WO 99/14185; WO 98/07685], and a synthetic method wherein quinic acid is used as a starting material [see Organic Process Research & Development, vol. 3, p. 266 (1999)] and the like are known.

The shikimic acid and quinic acid used as a starting material for the conventional synthetic method of ethyl (1β,5α,6β)-5-(1-ethylpropoxy)-7-oxabicyclo[4.1.0]hept-3-ene-3-carboxylate are produced in less amounts and expensive. As widely known, influenza often becomes an epidemic disease worldwide, and an anti-influenza drug is required to be economical and to be supplied in a large amount. The above-mentioned production methods are not necessarily advantageous as a production method of the intermediate for GS4104 under development as an anti-influenza drug from the industrial viewpoint, and there is a demand for a synthetic method capable of economical production in a large amount.

DISCLOSURE OF THE INVENTION

It is therefore an object of the present invention to provide a production method of a 5-oxy-7-oxabicyclo[4.1.0]hept-3-ene-3-carboxylic acid ester, such as ethyl (1β,5α,6β)-5-(1-ethylpropoxy)-7-oxabicyclo[4.1.0]hept-3-ene-3-carboxylate, useful as a synthetic intermediate for GS4104 under development as an anti-influenza drug, economically, industrially advantageously and efficiently in a large amount.

According to the present invention, the above-mentioned objects can be achieved by providing (1) a production method of a 5-oxy-7-oxabicyclo[4.1.0]hept-3-ene-3-carboxylic acid ester of the formula (X)

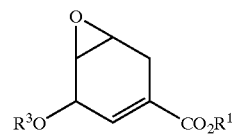

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents [hereinafter to be abbreviated as 5-oxy-7-oxabicyclo[4.1.0]hept-3-ene-3-carboxylic acid ester (X)], which comprises:

reacting a 2-halogeno-7-oxabicyclo[2.2.1]heptane-5,3-carbolactone of the formula (I)

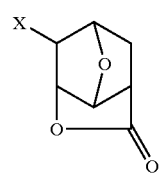

wherein X is a halogen atom [hereinafter to be abbreviated as halolactone (I)] with a base, reacting the resulting compound with alkyl halide optionally having substituents, cycloalkyl halide optionally having substituents, alkenyl halide optionally having substituents, aryl halide optionally having substituents or aralkyl halide optionally having substituents to give a 2,3-epoxy-7-oxabicyclo[2.2.1]heptane-5-carboxylic acid ester of the formula (III)

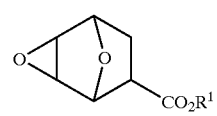

wherein $R^1$ is as defined above [hereinafter to be abbreviated as epoxy ester (III)], reacting the obtained epoxy ester (III) with a base to give a 5-hydroxy-7-oxabicyclo[4.1.0]hept-2-ene-3-carboxylic acid ester of the formula (IV)

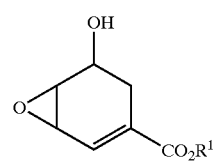

wherein $R^1$ is as defined above [hereinafter to be abbreviated as oxabicyclohept-2-ene (IV)], protecting a hydroxyl group of the obtained oxabicyclohept-2-ene (IV) to give a 5-oxy-7-oxabicyclo[4.1.0]hept-2-ene-3-carboxylic acid ester of the formula (V)

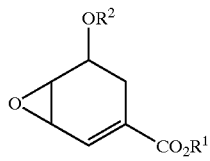

(V)

wherein R¹ is as defined above and R² is a hydroxyl-protecting group [hereinafter to be abbreviated as oxabicyclohept-2-ene (V)], reacting the obtained oxabicyclohept-2-ene (V) with an alcohol of the formula (VI)

(VI)

wherein R³ is as defined above [hereinafter to be abbreviated as alcohol (VI)] in the presence of a Lewis acid to give a 4-hydroxy-3,5-dioxy-1-cyclohexene-1-carboxylic acid ester of the formula (VII)

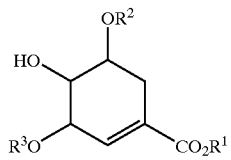

(VII)

wherein R¹, R² and R³ are as defined above [hereinafter to be abbreviated as cyclohexene ester (VII)], reacting the obtained cyclohexene ester (VII) with a sulfonylating agent in the presence of a base to give a 3,5-dioxy-4-sulfonyloxy-1-cyclohexene-1-carboxylic acid ester of the formula (VIII)

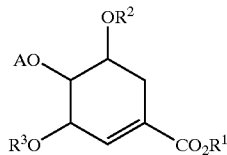

(VIII)

wherein R¹, R² and R³ are as defined above and A is an organic sulfonyl group [hereinafter to be abbreviated as cyclohexene ester (VIII)], removing the R² from the obtained cyclohexene ester (VIII) to give a 5-hydroxy-3-oxy-4-sulfonyloxy-1-cyclohexene-1-carboxylic acid ester of the formula (IX)

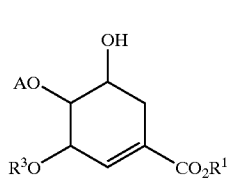

(IX)

wherein A, R¹ and R³ are as defined above [hereinafter to be abbreviated as hydroxy ester (IX)], and reacting the obtained hydroxy ester (IX) with a base, (2) a production method of 5-oxy-7-oxabicyclo[4.1.0]hept-3-ene-3-carboxylic acid ester (X), which comprises:

reacting halolactone (I) with a base to give a 2,3-epoxy-7-oxabicyclo[2.2.1]heptane-5-carboxylic acid of the formula (II)

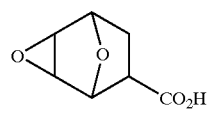

(II)

[hereinafter to be abbreviated as epoxy carboxylic acid (II)], reacting the obtained epoxy carboxylic acid (II) with an esterification agent to give epoxy ester (III), reacting the obtained epoxy ester (III) with a base to give oxabicyclohept-2-ene (IV), protecting a hydroxyl group of the obtained oxabicyclohept-2-ene (IV) to give oxabicyclohept-2-ene (V), reacting the obtained oxabicyclohept-2-ene (V) with an alcohol (VI) in the presence of a Lewis acid to give cyclohexene ester (VII), reacting the obtained cyclohexene ester (VII) with a sulfonylating agent in the presence of a base to give cyclohexene ester (VIII), removing the R² from the obtained cyclohexene ester (VIII) to give hydroxy ester (IX), and reacting the obtained hydroxy ester (IX) with a base, (3) a production method of epoxy carboxylic acid (II), which comprises reacting halolactone (I) with a base, (4) a production method of a 2,3-epoxy-7-oxabicyclo[2.2.1] heptane-5-carboxylic acid ester of the formula (III-1)

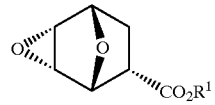

(III-1)

wherein R¹ is as defined above, or the formula (III-2)

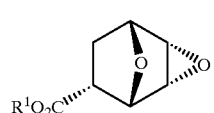

(III-2)

wherein R¹ is as defined above, which comprises reacting a 2,3-epoxy-7-oxabicyclo[2.2.1]heptane-5-carboxylic acid of the formula (II-1)

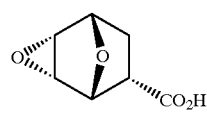

(II-1)

or the formula (II-2)

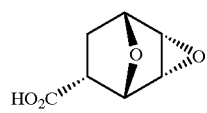

(II-2)

with an esterification agent, (5) a production method of epoxy ester (III), which comprises reacting halolactone (I) with a base, and
reacting the resulting compound with alkyl halide optionally having substituents, cycloalkyl halide optionally having substituents, alkenyl halide optionally having substituents, aryl halide optionally having substituents or aralkyl halide optionally having substituents, (6) a production method of oxabicyclohept-2-ene (IV), which comprises reacting epoxy ester (III) with a base, (7) a production method of cyclohexene ester (VII), which comprises protecting a hydroxyl group of oxabicyclohept-2-ene (IV) to give oxabicyclohept-2-ene (V), and
reacting the obtained oxabicyclohept-2-ene (V) with an alcohol (VI) in the presence of a Lewis acid, (8) a production method of cyclohexene ester (VII), which comprises reacting oxabicyclohept-2-ene (V) with an alcohol (VI) in the presence of a Lewis acid, (9) a production method of 5-oxy-7-oxabicyclo[4.1.0]hept-3-ene-3-carboxylic acid ester (X), which comprises reacting cyclohexene ester (VII) with a sulfonylating agent in the presence of a base to give cyclohexene ester (VIII), and
removing the $R^2$ from the obtained cyclohexene ester (VIII) to give hydroxy ester (IX), and
reacting the obtained hydroxy ester (IX) with a base,

(10) a production method of 5-oxy-7-oxabicyclo[4.1.0]hept-3-ene-3-carboxylic acid ester (X), which comprises removing the $R^2$ from a cyclohexene ester (VIII) to give hydroxy ester (IX), and
reacting the obtained hydroxy ester (IX) with a base,

(11) a production method of 5-oxy-7-oxabicyclo[4.1.0]hept-3-ene-3-carboxylic acid ester (X), which comprises reacting hydroxy ester (IX) with a base,

(12) an endo-2,3-epoxy-7-oxabicyclo[2.2.1]heptane-endo-5-carboxylic acid derivative of the formula (XI-1)

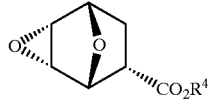

(XI-1)

wherein $R^4$ is a hydrogen atom, an alkyl group optionally having substituents, a cycloalkyl group optionally having substituents, an alkenyl group optionally having substituents, an aryl group optionally having substituents, an aralkyl group optionally having substituents or a metal capable of forming a salt with carboxylic acid, or the formula (XI-2)

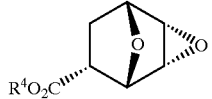

(XI-2)

wherein $R^4$ is as defined above, and

(13) a 3,4,5-trioxy-1-cyclohexene-1-carboxylic acid derivative of the formula (XII-1)

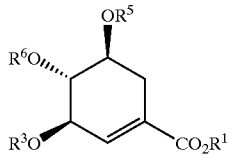

(XII-1)

wherein $R^1$ and $R^3$ are as defined above, and $R^5$ and $R^6$ are independently a hydrogen atom, an alkyl group optionally having substituents, a cycloalkyl group optionally having substituents, an alkenyl group optionally having substituents, an aryl group optionally having substituents, an aralkyl group optionally having substituents, a hydroxyl-protecting group or an organic sulfonyl group, or the formula (XII-2)

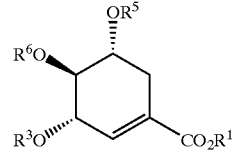

(XII-2)

wherein $R^1$, $R^3$, $R^5$ and $R^6$ are as defined above.

The alkyl group represented by $R^1$, $R^3$, $R^4$, $R^5$ and $R^6$ in the above-mentioned formulas, and $R^7$ in the formula (XIII) to be mentioned below is a straight chain or branched chain alkyl group preferably having 1 to 10, more preferably 1 to 6, carbon atoms. Examples thereof include methyl group, ethyl group, propyl group, isopropyl group, n-butyl group, isobutyl group, tert-butyl group, pentyl group, hexyl group and the like. These alkyl groups may have substituents, and examples of the substituent include alkoxyl group preferably having 1 to 10, more preferably 1 to 6, carbon atoms, such as methoxy group, ethoxy group, propoxy group, butoxy group and the like; halogen atom such as fluorine atom, chlorine atom, bromine atom and the like; cyano group; nitro group; and the like.

The cycloalkyl group represented by $R^1$, $R^3$, $R^4$, $R^5$ and $R^6$ in the above-mentioned formulas, and $R^7$ in the formula (XIII) to be mentioned below is cycloalkyl group preferably having 3 to 8 carbon atoms and is exemplified by cyclopentyl group, cyclohexyl group, cyclooctyl group and the like. The aryl group represented by $R^1$, $R^3$, $R^4$, $R^5$, $R^6$ and $R^7$ is aryl group preferably having 6 to 10 carbon atoms, and is exemplified by phenyl group, naphthyl group and the like. The aralkyl group represented by $R^1$, $R^3$, $R^4$, $R^5$, $R^6$ and $R^7$ is aralkyl group wherein the alkyl moiety is alkyl group preferably having 1 to 6 carbon atoms and the aryl moiety has 1 to 3 aryl groups defined above. Examples thereof include benzyl group, diphenylmethyl group, triphenylmethyl group, phenethyl group and the like. These cycloalkyl group, aryl group and aralkyl group may have substituents and examples of the substituent include alkyl group preferably having 1 to 6 carbon atoms such as methyl group, ethyl group, propyl group, isopropyl group, n-butyl group, isobutyl group, tert-butyl group and the like; alkoxyl group preferably having 1 to 6 carbon atoms such as methoxy group, ethoxy group, propoxy group, butoxy group and the like; halogen atom such as fluorine atom, chlorine atom, bromine atom and the like; cyano group; nitro group and the like. The alkenyl group represented by $R^1$, $R^3$, $R^4$, $R^5$, $R^6$ and $R^7$ is a straight chain or branched chain alkenyl group preferably having 2 to 10, more preferably 2 to 6 carbon atoms. Examples thereof include allyl group, isopropenyl group, 2-methylallyl group and the like. These alkenyl groups may have substituents and examples of the substituent include alkoxyl group preferably having 1 to 6 carbon atoms such as methoxy group, ethoxy group, propoxy group, butoxy group and the like; halogen atom such as fluorine atom, chlorine atom, bromine atom and the like; cyano group; nitro group; and the like.

The hydroxyl-protecting group represented by $R^2$, $R^5$ and $R^6$ in the above-mentioned formulas is free of any particular limitation as long as it is generally used for protecting the hydroxyl group, and is exemplified by acyl group such as formyl group, acetyl group, chloroacetyl group, trichloroacetyl group, trifluoroacetyl group, methoxyacetyl group, triphenylmethoxyacetyl group, propionyl group, butyryl group, benzoyl group and the like; tri-substituted silyl group such as trimethylsilyl group, triethylsilyl group, isopropyldimethylsilyl group, tert-butyldimethylsilyl group, tert-butyldiphenylsilyl group and the like; aralkyl group such as benzyl group, 2,4,6-trimethylbenzyl group, p-methoxybenzyl group, 3,5-dimethoxybenzyl group, p-nitrobenzyl group, o-nitrobenzyl group, o-chlorobenzyl group, p-chlorobenzyl group, o-bromobenzyl group, p-bromobenzyl group, 2,4-dichlorobenzyl group, p-cyanobenzyl group, m-chloro-p-acyloxybenzyl group, 9-anthrylmethyl group, diphenylmethyl group, phenyl(o-nitrophenyl)methyl group, di(2-pyridyl)methyl group, 4-pyridylmethyl group, triphenylmethyl group and the like; and the like.

The metal capable of forming a salt with carboxylic acid represented by $R^4$ in the above-mentioned formulas is free of any particular limitation as long as it is a metal that forms a salt with carboxylic acid, and is exemplified by alkali metal such as lithium, sodium, potassium and the like; alkaline earth metal such as magnesium, calcium and the like; transition metal such as iron, nickel, palladium, copper and the like; and the like.

The organic sulfonyl group represented by A, $R^5$ and $R^6$ in the above-mentioned formulas is free of any particular limitation as long as it is a sulfonyl group bonded with an organic group, and is exemplified by alkylsulfonyl group optionally having substituents, arylsulfonyl group optionally having substituents, aralkylsulfonyl group optionally having substituents and the like. The alkyl moiety of the alkylsulfonyl group is alkyl group preferably having 1 to 6 carbon atoms. The aryl moiety of the arylsulfonyl group is, for example, phenyl group. The aryl moiety of the aralkylsulfonyl group is, for example, phenyl group, and the alkyl moiety is alkyl group preferably having 1 to 6 carbon atoms. The alkylsulfonyl group may have substituents, and examples of the substituent include alkoxyl group (alkoxyl group preferably having 1 to 6 carbon atoms), halogen atom, cyano group, nitro group and the like. The arylsulfonyl group and aralkylsulfonyl group may have substituents on the aromatic ring thereof, and examples of the substituent include alkyl group (alkyl group preferably having 1 to 6 carbon atoms), alkoxyl group (alkoxyl group preferably having 1 to 6 carbon atoms), halogen atom, cyano group, nitro group and the like. The organic sulfonyl group represented by A, $R^5$ and $R^6$ is exemplified by methanesulfonyl group, ethanesulfonyl group, benzenesulfonyl group, toluenesulfonyl group, p-methoxybenzenesulfonyl group, 2,4,6-trimethylbenzenesulfonyl group, benzylsulfonyl group, p-methylbenzylsulfonyl group, trifluoromethanesulfonyl group and the like.

The halogen atom represented by X in the above-mentioned formulas is exemplified by iodine atom, bromine atom, chlorine atom, and fluorine atom.

The production method of 5-oxy-7-oxabicyclo[4.1.0]hept-3-ene-3-carboxylic acid ester (X) of the present invention is shown in the following scheme.

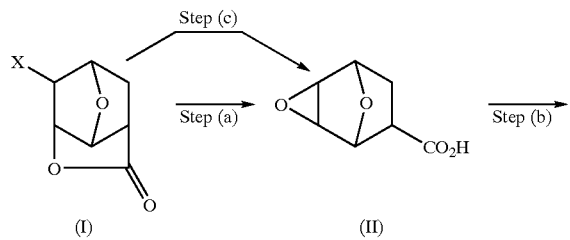

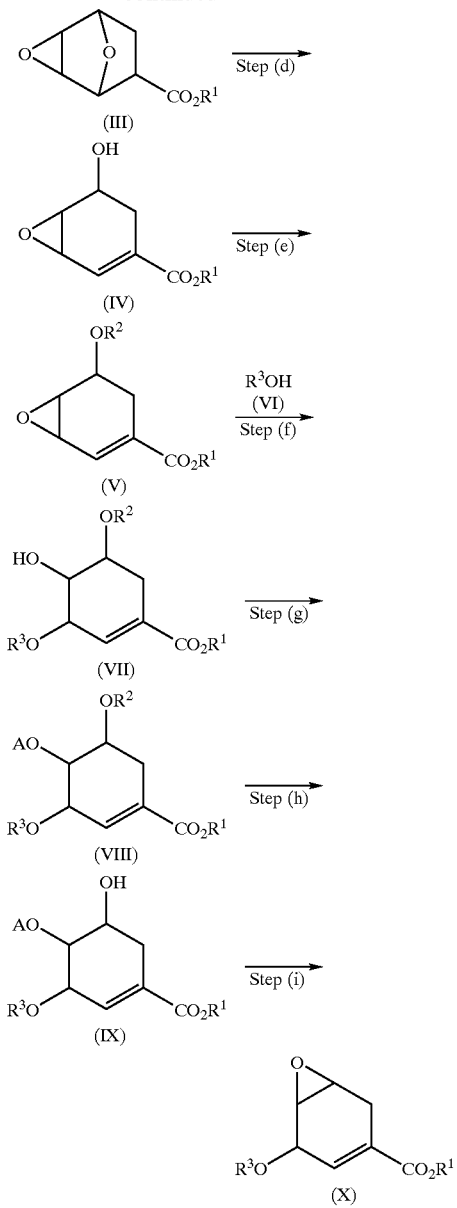

wherein $R^1$, $R^2$, $R^3$ and A are as defined above.

In the following, each step is explained.

(a): Step for Reacting Halolactone (I) with a Base to Give Epoxy Carboxylic Acid (II)

Examples of the base include alkali metal hydroxide such as lithium hydroxide, sodium hydroxide, potassium hydroxide and the like. Of these, potassium hydroxide is preferable. The amount of the base to be used is preferably 2 to 100 moles, more preferably 2 to 20 moles, per 1 mole of halolactone (I).

The reaction is preferably carried out in a solvent. The solvent to be used is free of any particular limitation as long as it does not adversely affect the reaction. Examples thereof include water; alcohol such as methanol, ethanol, propanol, butanol, tert-butanol and the like; aprotic polar solvent such as acetonitrile, N,N-dimethylformamide, 1,3-dimethyl-2-imidazolidinone and the like; a mixture of alcohol and aprotic polar solvent, a mixture of water and aprotic polar solvent and the like. The amount of the solvent to be used is free of any particular limitation, but it is generally preferably 1 to 100-fold weight, more preferably 1 to 50-fold weight, relative to halolactone (I).

The reaction temperature is preferably −20° C. to 150° C., more preferably 10° C. to 100° C. While the reaction time varies depending on the kind and the amount of halolactone (I), base and solvent, it is generally within the range of 1 to 12 hours.

The reaction is carried out by, for example, dissolving a base in a solvent, adjusting the solution to have a certain temperature, to which halolactone (I) is added, and stirring the mixture.

The epoxy carboxylic acid (II) thus obtained can be separated and purified according to a method generally employed for the separation and purification of organic compounds. For example, the reaction mixture is poured into an aqueous solution such as hydrochloric acid, sulfuric acid and the like, extracted with halogenated hydrocarbon such as dichloromethane and the like, ether such as diethyl ether, diisopropyl ether and the like, ester such as methyl acetate, ethyl acetate and the like; and the like, and the extract is concentrated and the obtained concentrate is purified by silica gel column chromatography and the like.

(b): Step for Reacting Epoxy Carboxylic Acid (II) with an Esterification Agent to Give Epoxy Ester (III)

The esterification agent is that capable of forming —$CO_2R^1$ in epoxy ester (III), such as alkyl orthoformate such as methyl orthoformate, ethyl orthoformate, propyl orthoformate, butyl orthoformate and the like; cycloalkyl orthoformate such as cyclopropyl orthoformate, cyclohexyl orthoformate and the like; alkenyl orthoformate such as allyl orthoformate and the like; aryl orthoformate such as phenyl orthoformate and the like; aralkyl orthoformate such as benzyl orthoformate and the like; alkyl orthoacetate such as methyl orthoacetate, ethyl orthoacetate, propyl orthoacetate, butyl orthoacetate and the like; cycloalkyl orthoacetate such as cyclopropyl orthoacetate, cyclohexyl orthoacetate and the like; alkenyl orthoacetate such as allyl orthoacetate and the like; aryl orthoacetate such as phenyl orthoacetate and the like; aralkyl orthoacetate such as benzyl orthoacetate and the like, and the like. These may have substituents such as those mentioned with regard to each group of the above-mentioned $R^1$. The amount of the esterification agent to be used is preferably 1 to 20 moles, more preferably 1 to 10 moles, per 1 mole of epoxy carboxylic acid (II).

The reaction can be carried out in the presence or absence of a solvent. The solvent to be used is free of any particular limitation as long as it does not adversely affect the reaction. Examples of the solvent include aliphatic hydrocarbon such as octane, decane and the like; aromatic hydrocarbon such as benzene, toluene, xylene, mesitylene and the like; ether such as diisopropyl ether, dioxane and the like; and the like. When a solvent is used, the amount thereof is free of any particular limitation. It is generally preferably 1 to 10-fold weight, more preferably 1 to 3-fold weight relative to epoxy carboxylic acid (II).

The reaction temperature is preferably 80–180° C., more preferably 120–160° C. While the reaction time varies depending on the kind and the amount of epoxy carboxylic acid (II), esterification agent and solvent, it is generally 1 to 6 hours.

The reaction is carried out by, for example, mixing epoxy carboxylic acid (II), esterification agent and as necessary solvent and stirring the mixture at a given temperature.

The epoxy ester (III) thus obtained can be separated and purified according to a method generally employed for the separation and purification of organic compounds. For example, the reaction mixture is poured into water, extracted with aliphatic hydrocarbon such as hexane, heptane, octane and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

(c): Step for Reacting Halolactone (I) with a Base, then with Alkyl Halide Optionally Having Substituents, Cycloalkyl Halide Optionally Having Substituents, Alkenyl Halide Optionally Having Substituents, Aryl Halide Optionally Having Substituents or Aralkyl Halide Optionally Having Substituents, as an Alkylating Agent to Give Epoxy Ester (III)

In this step, halolactone (I) is reacted with a base to form epoxy carboxylic acid (II) in the reaction zone, and the produced epoxy carboxylic acid (II) is sujected to the next reaction without isolation to give epoxy ester (III) in one pot.

Examples of the base include alkali metal hydroxide such as lithium hydroxide, sodium hydroxide, potassium hydroxide and the like. Of these, potassium hydroxide is preferable. The amount of the base to be used is preferably 2 to 100 moles, more preferably 2 to 20 moles, per 1 mole of halolactone (I).

The alkylating agent is that capable of forming —$CO_2R^1$ in epoxy ester (III), which is exemplified by alkyl halide such as methyl iodide, ethyl iodide, butyl iodide, octyl iodide, methyl bromide, ethyl bromide, butyl bromide, octyl bromide, methyl chloride, ethyl chloride, butyl chloride, octyl chloride and the like; cycloalkyl halide such as cyclopropyl iodide, cyclopentyl iodide, cyclohexyl iodide, cyclopropyl bromide, cyclopentyl bromide, cyclohexyl bromide, cyclopropyl chloride, cyclopentyl chloride, cyclohexyl chloride and the like; alkenyl halide such as allyl iodide, allyl bromide, allyl chloride and the like; aryl halide such as phenyl iodide, phenyl bromide, phenyl chloride and the like; aralkyl halide such as benzyl iodide, benzyl bromide, benzyl chloride and the like; and the like. These may have substituents as explained with regard to each group of $R^1$ mentioned above. The amount of the above-mentioned alkyl halide, cycloalkyl halide, alkenyl halide, aryl halide or aralkyl halide to be used is preferably 1 to 20 moles, more preferably 1 to 10 moles, per 1 mole of halolactone (I).

The reaction is preferably carried out in a solvent. The solvent to be used is free of any particular limitation as long as it does not adversely affect the reaction. Examples thereof include water; alcohol such as methanol, ethanol, propanol, butanol, tert-butanol and the like; aprotic polar solvent such as acetonitrile, N,N-dimethylformamide, 1,3-dimethyl-2-imidazolidinone and the like; a mixture of alcohol and aprotic polar solvent, a mixture of water and aprotic polar solvent and the like. The amount of the solvent to be used is free of any particular limitation, but it is generally preferably 1 to 100-fold weight, more preferably 1 to 50-fold weight, relative to halolactone (I).

The reaction temperature is preferably −20° C. to 150° C., more preferably 10° C. to 80° C. While the reaction time varies depending on the kind and the amount of halolactone (I), base, the above-mentioned alkyl halide, cycloalkyl halide, alkenyl halide, aryl halide or aralkyl halide and solvent, it is generally within the range of 1 to 12 hours.

The reaction proceeds by, for example, dissolving a base in a solvent and adjusting the solution to have a certain temperature, to which halolactone (I) is added to form epoxy carboxylic acid (II) in the reaction zone, then adding the aforementioned alkyl halide, cycloalkyl halide, alkenyl halide, aryl halide or aralkyl halide, which is followed by stirring.

The epoxy ester (III) thus obtained can be separated and purified according to a method generally employed for the separation and purification of organic compounds. For example, the reaction mixture is poured into water, extracted with aliphatic hydrocarbon such as hexane, heptane, octane and the like, halogenated hydrocarbon such as dichloromethane and the like, ether such as diethyl ether, diisopropyl ether and the like, ester such as methyl acetate, ethyl acetate and the like; and the like, and the extract is concentrated and the obtained concentrate is purified by distillation, silica gel column chromatography and the like.

(d): Step for Reacting Epoxy Ester (III) with a Base to Give Oxabicyclohept-2-ene (IV)

Examples of the base include alkali metal alkoxide such as sodium methoxide, potassium methoxide, sodium ethoxide, potassium ethoxide, sodium tert-butoxide, potassium tert-butoxide and the like; alkali metal organic base such as tert-butyllithium, lithium bis(trimethylsilyl)amide, sodium bis(trimethylsilyl)amide, potassium bis(trimethylsilyl)amide, lithium hexamethyldisilazane and the like. Of these, lithium bis(trimethylsilyl)amide and lithium hexamethyldisilazane are particularly preferable. The amount of the base to be used is preferably 1 to 20 moles, more preferably 1 to 5 moles, per 1 mole of epoxy ester (III).

The reaction is preferably carried out in a solvent. The solvent to be used is free of any particular limitation as long as it does not adversely affect the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; and the like. When a solvent is used, the amount of the solvent to be used is free of any particular limitation, but it is generally preferably 1 to 100-fold weight, more preferably 1 to 30-fold weight, relative to epoxy ester (III).

The reaction temperature is preferably −100 to 25° C., more preferably −70 to 0° C. While the reaction time varies depending on the kind and the amount of epoxy ester (III), base and solvent, it is generally within the range of 0.5 to 10 hours.

The reaction is carried out by, for example, dissolving a base in a solvent, adjusting the solution to have a certain temperature, to which epoxy ester (III) is added, and stirring the mixture.

The oxabicyclohept-2-ene (IV) thus obtained can be separated and purified according to a method generally employed for the separation and purification of organic compounds. For example, the reaction mixture is poured into water, extracted with aliphatic hydrocarbon such as hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

(e): Step for Protecting a Hydroxyl Group of Oxabicyclohept-2-ene (IV) to Give Oxabicyclohept-2-ene (V)

As the hydroxyl-protecting group, the protecting groups generally used for the protection of hydroxyl group can be used. Of these protecting groups, those stable under the reaction conditions, under which to produce cyclohexene ester (VII) in the next step (f) and which to produce cyclohexene ester (VIII) in the step (g) to be mentioned below, and capable of being quickly removed without impairing other moieties of hydroxy ester (IX) when the protecting group is to be removed in step (h) to be mentioned below, are particularly preferable. Examples of the hydroxyl-protecting group include acyl group such as formyl group, acetyl group, trifluoroacetyl group, propionyl group, butyryl group, benzoyl group and the like. Of these, acetyl group is particularly preferable. These hydroxyl-protecting groups can be introduced by a known method (T. W. Green, "Protective Groups in Organic Synthesis," John-Wiley & Sons, New York, 1981, pp 10–72).

The reaction is preferably carried out in a solvent. The solvent to be used is free of any particular limitation as long as it does not adversely affect the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; and the like. The amount of the solvent to be used is free of any particular limitation, but it is generally preferably 1 to 100-fold weight, more preferably 1 to 10-fold weight, relative to oxabicyclohept-2-ene (IV).

For example, acetyl group is introduced by reaction using 1–10 moles, preferably 1–3 moles, of acetic anhydride per 1 mole of oxabicyclohept-2-ene (IV), in the presence of 1–10 moles, preferably 1–3 moles, of a base such as an amine such as triethylamine, pyridine, collidin, lutidine, 4-dimethylaminopyridine and the like; alkaline metal hydride such as sodium hydride, potassium hydride and the like; alkaline metal carbonate such as sodium carbonate, potassium carbonate and the like, per 1 mole of oxabicyclohept-2-ene (IV). In this case, it is also possible to carry out the reaction of the aforementioned step (d) and this step in one phase using epoxy ester (III) as a starting material instead of oxabicyclohept-2-ene (IV).

The oxabicyclohept-2-ene (V) thus obtained can be separated and purified according to a method generally employed for the separation and purification of organic compounds. For example, the reaction mixture is poured into water, extracted with aliphatic hydrocarbon such as hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

(f): Step for Reacting oxabicyclohept-2-ene (V) with Alcohol (VI) in the Presence of Lewis Acid to Give Cyclohexene Ester (VII)

The alcohol (VI) can form —$OR^3$ in cyclohexene ester (VII), and is exemplified by primary or secondary alkylalcohol such as methanol, ethanol, 1-propanol, 1-octanol, isopropanol, 2-butanol, 2-pentanol, 3-pentanol and the like; cycloalkylalcohol such as secondary alcohol such as cyclopentanol, cyclohexanol and the like; alkenylalcohol such as allylalcohol and the like; arylalcohol such as phenol, naphthol and the like; aralkylalcohol such as benzyl alcohol and the like. These may have substituents such as those explained with regard to each group of the above-mentioned $R^3$. Of these, the use of 3-pentanol as alcohol (VI) is particularly preferable from the viewpoint of synthesis of ethyl (1β,5α,6β)-5-(1-ethylpropoxy)-7-oxabicyclo[4.1.0]hept-3-ene-3-carboxylate, which is a synthetic intermediate for GS4104. The amount of the alcohol (VI) to be used is preferably 1 to 200 moles, more preferably 1 to 100 moles, per 1 mole of oxabicyclohept-2-ene (V).

Examples of the Lewis acid include boron trifluoride-etherate, aluminum chloride, zinc chloride, zinc iodide, titanium tetrachloride and the like. The amount of the Lewis acid to be used is preferably 0.1 to 30 moles, more preferably 1 to 10 moles, per 1 mole of oxabicyclohept-2-ene (V).

The reaction can be carried out in the presence or absence of a solvent. The solvent to be used is free of any particular limitation as long as it does not adversely affect the reaction. Examples of the solvent include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, 1,2-dichloroethane and the like; and the like. When a solvent is used, the amount thereof is free of any particular limitation. It is generally preferably 1 to 100-fold weight, more preferably 1 to 10-fold weight relative to oxabicyclohept-2-ene (V).

The reaction temperature is preferably 0–100° C., more preferably 10–80° C. While the reaction time varies depending on the kind and the amount of oxabicyclohept-2-ene (V), alcohol (VI), Lewis acid and solvent, it is generally 0.5 to 10 hours.

The reaction is carried out by, for example, mixing oxabicyclohept-2-ene (V), alcohol (VI), Lewis acid and a solvent as necessary and stirring the mixture at a given temperature.

The cyclohexene ester (VII) thus obtained can be separated and purified according to a method generally employed for the separation and purification of organic compounds. For example, the reaction mixture is poured into water, extracted with aliphatic hydrocarbon such as hexane and the like; aromatic hydrocarbon such as toluene and the like; halogenated hydrocarbon such as dichloromethane and the like; ether such as diethyl ether, diisopropyl ether and the like; and the like, and the extract is concentrated and the obtained concentrate is purified by distillation, silica gel column chromatography and the like.

(g): Step for Reacting Cyclohexene Ester (VII) with a Sulfonylating Agent in the Presence of a Base to Give Cyclohexene Ester (VIII)

Examples of the base include tertiary amine such as trimethylamine, triethylamine, tripropylamine, tributylamine, trioctylamine, pyridine, collidine, lutidine and the like; alkaline metal hydride such as sodium hydride, potassium hydride and the like; alkaline metal carbonate such as sodium carbonate, potassium carbonate and the like; and the like. Of these, triethylamine, pyridine and lutidine are preferable. The amount of the base to be used is preferably 1 to 10 moles, more preferably 1 to 5 moles, per 1 mole of cyclohexene ester (VII).

Examples of the sulfonylating agent include organic sulfonyl halide such as alkylsulfonyl halide optionally having substituents such as methanesulfonyl chloride, methanesulfonyl fluoride, ethanesulfonyl chloride, ethanesulfonyl bromide, trifluoromethanesulfonyl chloride and the like; arylsulfonyl halide optionally having substituents such as benzenesulfonyl chloride, benzenesulfonyl bromide, benzenesulfonyl fluoride, toluenesulfonyl chloride, toluenesulfonyl bromide, toluenesulfonyl fluoride, p-methoxybenzenesulfonyl chloride, 2,4,6-trimethylbenzenesulfonyl chloride and the like; aralkylsulfonyl halide optionally having substituents such as benzylsulfonyl chloride, p-methylbenzylsulfonyl chloride and the like; organic sulfonic anhydride such as alkylsulfonic anhydride optionally having substituents such as methanesulfonic anhydride, trifluoromethanesulfonic anhydride and the like; arylsulfonic anhydride optionally having substituents such as p-toluenesulfonic anhydride and the like; aralkylsulfonic anhydride optionally having substituents such as benzylsulfonic anhydride and the like; and the like.

The amount of the sulfonylating agent to be used is preferably 1 to 10 moles, more preferably 1 to 5 moles, per 1 mole of cyclohexene ester (VII).

The reaction is preferably carried out in a solvent. The solvent to be used is free of any particular limitation as long as it does not adversely affect the reaction. Examples thereof include aliphatic hydrocarbon such as hexane, heptane, octane and the like; aromatic hydrocarbon such as benzene, toluene, xylene, mesitylene and the like; ether such as diethyl ether, diisopropyl ether, tetrahydrofuran, dioxane and the like; halogenated hydrocarbon such as dichloromethane, chloroform, carbon tetrachloride, 1,2-dichloroethane and the like; and the like. The amount of the solvent to be used is free of any particular limitation, but it is generally preferably 1 to 100-fold weight, more preferably 1 to 10-fold weight, relative to cyclohexene ester (VII).

The reaction temperature is preferably −20° C. to 50° C., more preferably 10° C. to 30° C. While the reaction time varies depending on the kind and the amount of cyclohexene ester (VII), base, sulfonylating agent and solvent, it is generally within the range of 0.5 to 10 hours.

The reaction is carried out by, for example, dissolving cyclohexene ester (VII) and a base in a solvent, adjusting the solution to have a certain temperature, to which a sulfonylating agent is added, and stirring the mixture.

The cyclohexene ester (VIII) thus obtained can be separated and purified according to a method generally employed for the separation and purification of organic compounds. For example, the reaction mixture is poured into water, extracted with aliphatic hydrocarbon such as hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

(h): Step for Removing $R^2$ from Cyclohexene Ester (VIII) to Give Hydroxy Ester (IX)

The hydroxyl-protecting group represented by $R^2$ can be removed from cyclohexene ester (VIII) according to a known method (T. W. Green, "Protective Groups in Organic Synthesis," John-Wiley & Sons, New York, 1981, pp 10–72).

The reaction is preferably carried out in a solvent. The solvent to be used is free of any particular limitation as long as it does not adversely affect the reaction. Examples of the solvent include aliphatic hydrocarbon such as hexane, heptane, octane and the like; aromatic hydrocarbon such as benzene, toluene, xylene, mesitylene and the like; alcohol such as methanol, ethanol, propanol, butanol, tert-butanol and the like; ether such as diethyl ether, diisopropyl ether, tetrahydrofuran, dioxane and the like; and the like. The amount of the solvent to be used is free of any particular limitation. It is generally preferably 1 to 100-fold weight, more preferably 1 to 10-fold weight relative to cyclohexene ester (VIII).

The hydroxy ester (IX) thus obtained can be separated and purified according to a method generally employed for the separation and purification of organic compounds. For example, the reaction mixture is poured into water, extracted with aliphatic hydrocarbon such as hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

When the hydroxyl-protecting group represented by $R^2$ is an acyl group such as acetyl group, it can be removed using alcohol, such as methanol, ethanol and the like, as a solvent and an alkali metal carbonate, such as sodium carbonate, potassium carbonate and the like, as a base, in which case the reaction of hydroxy ester (IX) with a base, which is to be mentioned in the following step (i), is simultaneously conducted, thereby affording 5-oxy-7-oxabicyclo[4.1.0] hept-3-ene-3-carboxylic acid ester (X) by a one phase reaction.

(i): Step for Reacting Hydroxy Ester (IX) with a Base to Give 5-oxy-7-oxabicyclo[4.1.0]hept-3-ene-3-carboxylic Acid Ester (X)

Examples of the base include tertiary amine such as trimethylamine, triethylamine, tripropylamine, tributylamine, trioctylamine, pyridine, collidine, lutidine and the like; alkaline metal hydride such as sodium hydride, potassium hydride and the like; alkaline metal carbonate such as sodium carbonate, potassium carbonate and the like; and the like. The amount of the base to be used is preferably 1 to 10 moles, more preferably 1 to 5 moles, per 1 mole of hydroxy ester (IX).

The reaction is preferably carried out in a solvent. The solvent to be used is free of any particular limitation as long as it does not adversely affect the reaction. Examples of the solvent include aliphatic hydrocarbon such as hexane, heptane, octane and the like; aromatic hydrocarbon such as benzene, toluene, xylene, mesitylene and the like; alcohol such as methanol, ethanol, propanol, butanol, tert-butanol and the like; ether such as diethyl ether, diisopropyl ether, tetrahydrofuran, dioxane and the like; and the like. The amount of the solvent to be used is free of any particular limitation, but it is generally preferably 1 to 100-fold weight, more preferably 1 to 10-fold weight relative to hydroxy ester (IX).

The reaction temperature is preferably −20° C. to 50° C., more preferably 10° C. to 30° C. While the reaction time varies depending on the kind and the amount of hydroxy ester (IX), base and solvent, it is generally within the range of 0.5 to 10 hours.

The reaction is carried out by, for example, dissolving hydroxy ester (IX) in a solvent, adjusting the solution to have a certain temperature, to which a base is added, and stirring the mixture.

The 5-oxy-7-oxabicyclo[4.1.0]hept-3-ene-3-carboxylic acid ester (X) thus obtained can be separated and purified according to a method generally employed for the separation and purification of organic compounds. For example, the reaction mixture is poured into water, extracted with aliphatic hydrocarbon such as hexane and the like, aromatic hydrocarbon such as toluene and the like, halogenated hydrocarbon such as dichloromethane and the like, ether such as diethyl ether, diisopropyl ether and the like; and the like, and the extract is concentrated and the obtained concentrate is purified by distillation, silica gel column chromatography and the like.

The halolactone (I), which is a starting material for the present invention, can be produced as shown in Reference Examples 1–4 to be mentioned below, wherein furan and acrylic acid ester of the formula (XIII)

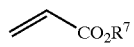

(XIII)

wherein $R^7$ is an alkyl group optionally having substituents, a cycloalkyl group optionally having substituents, an alkenyl group optionally having substituents, an aryl group optionally having substituents or an aralkyl group optionally having substituents, are subjected to a Diels-Alder reaction in the presence of a Lewis acid, such as zinc iodide, zinc chloride, titanium tetrachloride and the like [see Tetrahedron Letters, vol. 23, p. 5299 (1982)], the obtained compound is reacted with a strong base, such as sodium hydroxide, potassium hydroxide and the like, to convert the same into a carboxylic acid, which is then reacted with halogen, such as iodine, bromine and the like, in the presence of a base, such as sodium hydrogen carbonate, potassium hydrogen carbonate and the like [see Journal of the Chemical Society, Chemical Communications (J. Chem. Soc. Chem. Commun.), p. 406 (1992)].

According to the method described in The Journal of Organic Chemistry (J. Org. Chem.), vol. 63, p. 4545 (1998), GS4104 can be synthesized from 5-oxy-7-oxabicyclo[4.1.0] hept-3-ene-3-carboxylic acid ester (X), such as ethyl (1β, 5α,6β)-5-(1-ethylpropoxy)-7-oxabicyclo[4.1.0]hept-3-ene-3-carboxylate obtained by the method of the present invention.

According to the method of the present invention, an endo-2,3-epoxy-7-oxabicyclo[2.2.1]heptane-endo-5-carboxylic acid derivative of the formula (XI-1)

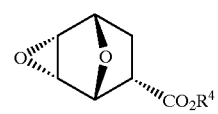

(XI-1)

wherein $R^4$ is a hydrogen atom, an alkyl group optionally having substituents, a cycloalkyl group optionally having substituents, an alkenyl group optionally having substituents, an aryl group optionally having substituents, an aralkyl group optionally having substituents or a metal capable of forming a carboxylic acid salt, or the formula (XI-2)

(XI-2)

wherein $R^4$ is as defined above, is an important intermediate. The compound of the formula (XI-1) or formula (XI-2) becomes a compound of the formula (II-1) or formula (II-2), respectively, when $R^4$ is a hydrogen atom, and becomes a compound of the formula (III-1) or formula (III-2), respectively, when $R^4$ is $R^1$.

In the method of the present invention, 3,4,5-trioxy-1-cyclohexene-1-carboxylic acid derivative of the formula (XII-1)

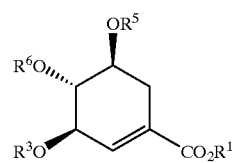

(XII-1)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, $R^5$ and $R^6$ are independently a hydrogen atom, an alkyl group optionally having substituents, a cycloalkyl group optionally having substituents, an alkenyl group optionally having substituents, an aryl group optionally having substituents, an aralkyl group optionally having substituents, a hydroxyl-protecting group or an organic sulfonyl group, or the formula (XII-2)

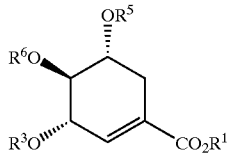

(XII-2)

wherein $R^1$, $R^3$, $R^5$ and $R^6$ are as defined above, is also an important intermediate. As used herein, a compound of the formula (XII-1) or formula (XII-2) corresponds to cyclohexene ester (VII) having the same configuration as the formula (XII-1) or (XII-2), when $R^5$ is $R^2$ and $R^6$ is hydrogen atom, respectively; corresponds to cyclohexene ester (VIII) having the same configuration as the formula (XII-1) or (XII-2), when $R^5$ is $R^2$ and $R^6$ is A; and corresponds to hydroxy ester (IX) having the same configuration as the formula (XII-1) or (XII-2), when $R^5$ is hydrogen atom and $R^6$ is A.

EXAMPLES

The present invention is described in more detail by means of the following Examples, which are not to be construed as limitative.

Reference Example 1

Synthesis of Methyl 7-oxabicyclo[2.2.1]hept-2-ene-endo-5-carboxylate

Methyl acrylate (9.0 ml, 100 mmol) was added to furan (10 ml, 142 mmol) and the mixture was cooled to −10° C. To this solution was dropwise added a solution (40 ml, 1 mol/l, 40 mmol) of titanium tetrachloride in dichloromethane at −10° C. over 45 min, and the mixture was stirred at −10° C. for 2 hr. The reaction mixture was slowly added to a cooled saturated aqueous sodium hydrogen carbonate solution and the mixture was stirred for 30 min. The precipitated impurity was filtered off, and the organic layer and the aqueous layer were separated. The aqueous layer was extracted twice with dichloromethane (50 ml). The organic layers were combined and dried over anhydrous sodium sulfate. The solvent was distilled away and the residue was purified by silica gel column chromatography (ethyl acetate:hexane=1:10) to give methyl 7-oxabicyclo[2.2.1]hept-2-ene-endo-5-carboxylate (5.95 g, 38.6 mmol, yield 38.6%) and methyl 7-oxabicyclo[2.2.1]hept-2-ene-exo-5-carboxylate (2.55 g, 16.6 mmol, yield 16.6%). The endo form:exo form ratio thus produced was 7:3.

$^1$H-NMR(250 MHz):
endo form: δ=6.46–6.43 (1H, m), 6.25–6.22 (1H, m), 5.18–5.16 (1H, m), 5.03–5.01 (1H, m), 3.65 (3H, s), 3.18–3.05 (1H, m), 2.18–2.02 (1H, m), 1.68–1.52 (1H, m).
exo form: δ=6.42–6.32 (2H, m), 5.19 (1H, s), 5.08 (1H, d, J=4.5 Hz), 3.73 (3H, s), 2.50–2.40 (1H, m), 2.25–2.15 (1H, m), 1.63–1.55 (1H, m).

Reference Example 2

Synthesis of 7-oxabicyclo[2.2.1]hept-2-ene-endo-5-carboxylic Acid

Methyl 7-oxabicyclo[2.2.1]hept-2-ene-endo-5-carboxylate (50.5 g, 328 mmol) obtained according to the method of Reference Example 1 was cooled to 5° C., and an aqueous solution of sodium hydroxide (20.3 g, 507 mmol) in distilled water (182 ml) was dropwise added over 15 min. After the dropwise addition, the reaction mixture was warmed to room temperature over 30 min and stirred at room temperature for 2 hr. To the reaction mixture was added 6N hydrochloric acid (140 ml) to adjust to pH <1, and the mixture was extracted 4 times with chloroform (100 ml). The organic layers were combined and dried over anhydrous sodium sulfate. The solvent was distilled away and the residue was purified by silica gel column chromatography (ethyl acetate:hexane=1:1) to give the objective product (40.2 g, 287 mmol, yield 87.5%).

$^1$H-NMR(250 MHz): δ=7.12–7.03 (1H, m), 6.31–6.18 (2H, m), 4.45–4.32 (1H, m), 4.23 (2H, q, J=7.2 Hz), 3.00–2.85 (1H, m), 2.71–2.54 (1H, m), 1.58 (1H, s), 1.31 (3H, t, J=7.2 Hz)

Reference Example 3

Synthesis of exo-2-iodo-7-oxabicyclo[2.2.1]heptane-endo-5,3-carbolactone

7-Oxabicyclo[2.2.1]hept-2-ene-endo-5-carboxylic acid (1.40 g, 10.0 mmol) obtained in Reference Example 2, iodine (5.1 g, 20 mmol) and sodium iodide (15 g, 0.1 mol) were dissolved in 5% aqueous sodium hydrogen carbonate solution (20 ml) and the mixture was stirred at room temperature for 12 hr. To the reaction mixture was added 10% aqueous sodium thiosulfate solution until the red color disappeared. The reaction mixture was extracted with dichloromethane, washed with saturated brine (20 ml) and dried over anhydrous sodium sulfate. The solvent was distilled away and the residue was purified by recrystallization (ethyl acetate:hexane=1:10) to give the objective product (2.47 g, 9.26 mmol, yield 92.6%).

IR(neat): 3020, 1795, 1448, 1348, 1321, 1215, 1184, 1024 cm$^{-1}$.

$^1$H-NMR(250 MHz): δ=5.39 (1H, t, J=4.5 Hz), 5.13 (1H, d, J=4.5 Hz), 4.82 (1H, d, J=4.5 Hz), 3.94 (1H, s), 2.80–2.75 (1H, m), 2.22–2.16 (2H, m).

EIMS m/z:266(M$^+$), 139[(M-I)$^+$], 127, 111, 83.

HRMS calcd for $C_7H_7O_3I$(M$^+$):265.9440. Found m/z=265.9445.

Reference Example 4

Synthesis of exo-2-bromo-7-oxabicyclo[2.2.1]heptane-endo-5,3-carbolactone 7-oxabicyclo[2.2.1]hept-2-ene-endo-5-carboxylic acid (5.00 g, 35.7 mmol) obtained in Reference Example 2 was dissolved in water (32 g) and sodium hydrogen carbonate (3.00 g, 35.7 mmol) was added by small portions while paying attention to foaming. After foaming disappeared, bromine (5.70 g, 35.7 mmol) was added dropwise over 5 min and the mixture was stirred at room temperature for 2 hr. The reaction mixture was extracted with ethyl acetate, washed with saturated aqueous sodium thiosulfate solution (100 ml) and dried over anhydrous sodium sulfate. The solvent was distilled away and the residue was purified by recrystallization (ethyl acetate) to give the objective product (7.00 g, 32.0 mmol, yield 89.6%).

$^1$H-NMR(270 MHz): δ=5.43 (1H, t, J=5.0 Hz), 4.97 (1H, d, J=5.0 Hz), 4.78 (1H, d, J=5.0 Hz), 3.94 (1H, s), 2.81–2.75 (1H, m), 2.08–2.37 (2H, m).

Example 1

Synthesis of endo-2,3-epoxy-7-oxabicyclo[2.2.1]heptane-endo-5-carboxylic acid

Potassium hydroxide (0.63 g, 11.22 mmol) was dissolved in a mixture of methanol (2.5 ml) and N,N- dimethylformamide (17.5 ml). To this solution was added exo-2-iodo-7-oxabicyclo[2.2.1]heptane-endo-5,3-carbolactone (0.5 g, 1.87 mmol) obtained in Reference Example 3, and the mixture was stirred at room temperature for 2.5 hr. To the reaction mixture was added 3% aqueous hydrochloric acid solution (15 ml) for neutralization. The mixture was extracted with dichloromethane, and the organic layer was washed with saturated brine and dried over anhydrous sodium sulfate. The solvent was distilled away and the residue was purified by silica gel column chromatography (ethyl acetate:hexane=1:1) to give the objective product (0.292 g, 1.86 mmol, yield 99.7%).

IR(neat): 3020, 2974, 2627, 1707, 1421, 1304, 1248, 1215 $cm^{-1}$.

$^1$H-NMR(250 MHz): δ=9.40–8.10 (1H, bs), 4.72–4.69 (1H, m), 4.55–4.52 (1H, m), 4.15–4.13 (1H, m), 4.06–4.03 (1H, m), 3.02–2.94 (1H, m), 2.13–1.92 (1H, m).

EIMS m/z: 156($M^+$), 139, 127, 110, 99.

HRMS calcd for $C_7H_8O_4(M^+)$: 156.0423, Found m/z= 156.0421.

Example 2

Synthesis of endo-2,3-epoxy-7-oxabicyclo[2.2.1]heptane-endo-5-carboxylic acid

Potassium hydroxide (1.55 g, 23.9 mmol) was dissolved in water (3.5 g) and to this solution was added exo-2-bromo-7-oxabicyclo[2.2.1]heptane-endo-5,3-carbolactone (2.5 g, 11.4 mmol) obtained in Reference Example 4. The mixture was stirred at 80° C. for 3 hr. To the reaction mixture was added 0.5M aqueous sulfuric acid solution (14 ml) to acidify the reaction mixture. The mixture was extracted with ethyl acetate, and the organic layer was washed with saturated brine and dried over anhydrous sodium sulfate. The solvent was distilled away and the residue was purified by silica gel column chromatography (ethyl acetate:hexane=1:1) to give the objective product (1.64 g, 10.5 mmol, yield 92.1%).

IR(neat): 3020, 2974, 2627, 1707, 1421, 1304, 1248, 1215 $cm^{-1}$.

H-NMR(250 MHz): δ=9.40–8.10 (1H, bs), 4.72–4.69 (1H, m), 4.55–4.52 (1H, m), 4.15–4.13 (1H, m), 4.06–4.03 (1H, m), 3.02–2.94 (1H, m), 2.13–1.92 (1H, m).

EIMS m/z: 156($M^+$), 139, 127, 110, 99.

HRMS calcd for $C_7H_8O_4(M^+)$: 156.0423, Found m/z= 156.0421.

Example 3

Synthesis of ethyl endo-2,3-epoxy-7-oxabicyclo[2.2.1]heptane-endo-5-carboxylate

To endo-2,3-epoxy-7-oxabicyclo[2.2.1]heptane-endo-5-carboxylic acid (0.146 g, 0.932 mmol) obtained in Example 1 was added triethyl orthoacetate (0.76 g, 4.66 mmol), and the mixture was stirred at 140° C. for 3 hr. The reaction mixture was concentrated and the residue was purified by silica gel column chromatography (ethyl acetate:hexane= 1:5) to give the objective product (0.171 g, 0.927 mmol, yield 99.4%).

IR(neat): 2982, 1732, 1450, 1369, 1334, 1298, 1219, 1041 $cm^{-1}$.

$^1$H-NMR(250 MHz): δ=4.70–4.68 (1H, m), 4.52–4.50 (1H, m), 4.20 (2H, q, J=7.2 Hz), 4.12–4.09 (1H, m), 4.03–4.00 (1H, m), 2.95–2.82 (1H, m), 2.11–1.96 (1H, m), 1.29(3H, t, J=7.2 Hz).

EIMS m/z: 184($M^+$), 166, 155, 139, 127, 110, 99.

HRMS calcd for $C_9H_{12}O_4(M^+)$: 184.0736, Found m/z= 184.0736.

Example 4

Synthesis of ethyl endo-2,3-epoxy-7-oxabicyclo[2.2.1]heptane-endo-5-carboxylate

Potassium hydroxide (0.37 g, 5.61 mmol) was dissolved in a mixture of methanol (2.5 ml) and N,N-dimethylformamide (17.5 ml). Exo-2-iodo-7-oxabicyclo[2.2.1]heptane-endo-5,3-carbolactone (0.5 g, 1.87 mmol) obtained in Reference Example 3 was added and the mixture was stirred at room temperature for 3 hr. Methanol was distilled away and to the reaction mixture was added ethyl iodide (0.96 g, 6.17 mmol). The mixture was stirred at room temperature for 6 hr. To the reaction mixture was added 1N aqueous hydrochloric acid solution (50 ml), and the mixture was extracted 8 times with ethyl acetate (20 ml). The organic layer was washed with saturated brine and dried over anhydrous sodium sulfate. The solvent was distilled away and the residue was purified by silica gel column chromatography (ethyl acetate:hexane=1:5) to give the objective product (0.33 g, 1.79 mmol, yield 95.9%).

IR(neat): 2982, 1732, 1450, 1369, 1334, 1298, 1219, 1041 $cm^{-1}$.

$^1$H-NMR(250 MHz): δ=4.70–4.68 (1H, m), 4.52–4.50 (1H, m), 4.20 (2H, q, J=7.2 Hz), 4.12–4.09 (1H, m), 4.03–4.00 (1H, m), 2.95–2.82 (1H, m), 2.11–1.96 (1H, m), 1.29 (3H, t, J=7.2 Hz).

EIMS m/z: 184($M^+$), 166, 155, 139, 127, 110, 99.

HRMS calcd for $C_9H_{12}O_4(M^+)$: 184.0736, Found m/z= 184.0736.

Example 5

Synthesis of ethyl (1α,5α,6α)-5-hydroxy-7-oxabicyclo[4.1.0]hept-2-ene-3-carboxylate To a solution (0.32 ml, 1.0 mol/l, 0.32 mmol) of lithium hexamethyldisilazane in tetrahydrofuran was added tetrahydrofuran (1 ml) and the mixture was cooled to −78° C. Thereto was dropwise added a solution of ethyl endo-2,3-epoxy-7-oxabicyclo[2.2.1]heptane-endo-5-carboxylate (53 mg, 0.287 mmol) obtained in Example 3 in tetrahydrofuran (1 ml). After the dropwise addition, the mixture was stirred at −10° C. for 1 hr. To the reaction mixture was added saturated aqueous ammonium chloride solution (5 ml) and the mixture was extracted with dichloromethane. The organic layer was washed with saturated brine (5 ml) and dried over anhydrous sodium sulfate. The solvent was distilled away and the residue was purified by silica gel column chromatography (ethyl acetate:hexane=1:5) to give the objective product (51.7 mg, 0.28 mmol, yield 97.5%).

IR(neat): 3445, 2984, 2935, 1712, 1645, 1417, 1386, 1367, 1263, 1207 $cm^{-1}$.

$^1$H-NMR(250 MHz): δ=7.16–7.13 (1H, m), 4.57–4.55 (1H, m), 4.21 (2H, q, J=7.2 Hz), 3.59–3.58 (1H, m), 3.50–3.47 (1H, m), 2.86–2.79 (1H, m), 2.37–2.22 (1H, m), 1.30 (3H, t, J=7.2 Hz).

EIMS m/z: 166[$(M-H_2O)^+$], 155, 138, 121, 110, 97.

HRMS calcd for $C_9H_{10}O_3[(M-H_2O)^+]$:166.0630; Found m/z=166.0645.

Example 6

Synthesis of ethyl (1α,5α,6α)-5-acetoxy-7-oxabicyclo[4.1.0]hept-2-ene-3-carboxylate Ethyl (1α,5α,6α)-5-hydroxy-7-oxabicyclo[4.1.0]hept-2-ene-3-carboxylate (15 mg, 0.081 mmol) obtained in Example 5 was dissolved in dichloromethane (0.5 ml), and acetic anhydride (12.4 mg, 0.122 mmol), triethylamine (12.4 mg, 0.122 mmol) and 4-dimethylaminopyridine (1 mg, 0.008 mmol) were added. The mixture was stirred at room temperature for 30 min. After the completion of the reaction, the solvent was distilled away and the residue was purified by silica gel column chromatography (ethyl acetate:hexane= 1:5) to give the objective product (15.6 mg, 0.069 mmol, yield 85.1%).

IR(neat): 2984, 1738, 1714, 1649, 1425, 1369, 1261, 1205, 1097, 1028 cm$^{-1}$.

$^1$H-NMR(250 MHz): δ=7.18–7.12 (1H, m), 5.67–5.60 (1H, m), 4.21 (2H, q, J=7.2 Hz), 3.63–3.60 (1H, m), 3.52–3.49 (1H, m), 2.76–2.85 (1H, m), 2.41–2.29 (1H, m), 2.04 (3H, s), 1.31 (3H, t, J=7.2 Hz).

Example 7

Synthesis of ethyl (1α,5α,6α)-5-acetoxy-7-oxabicyclo[4.1.0]hept-2-ene-3-carboxylate A solution (11 ml, 11 mmol) of 1.0 mol/l lithium hexamethyldisilazane in tetrahydrofuran was cooled to -30° C. Thereto was dropwise added ethyl endo-2,3-epoxy-7-oxabicyclo[2.2.1]heptane-endo-5-carboxylate (1.84 g, 10 mmol) obtained in Example 3 in tetrahydrofuran (5 ml). After the completion of the dropwise addition, the mixture was stirred at +30° C. for 1 hr. To the reaction mixture was added acetic anhydride (1.328 g, 13 mmol) and the mixture was warmed to room temperature and stirred for 3 hr. To the reaction mixture was added saturated aqueous ammonium chloride solution (30 ml) at room temperature, and the mixture was extracted with ethyl acetate (50 ml). The organic layer was dried over anhydrous sodium sulfate. The solvent was distilled away and the residue was purified by silica gel column chromatography (ethyl acetate:hexane= 1:5) to give the objective product (1.808 mg, 0.80 mmol, yield 80.0%).

IR(neat): 2984, 1738, 1714, 1649, 1425, 1369, 1261, 1205, 1097, 1028 cm$^{-1}$.

$^1$H-NMR(250 MHz): δ=7.18–7.12 (1H, m), 5.67–5.60 (1H, m), 4.21 (2H, q, J=7.2 Hz), 3.63–3.60 (1H, m), 3.52–3.49 (1H, m), 2.76–2.85 (1H, m), 2.41–2.29 (1H, m), 2.04 (3H, s), 1.31 (3H, t, J=25 7.2 Hz).

Example 8

Synthesis of ethyl (3α,5β,5α)-3-(1-ethylpropoxy)-4-hydroxy-5-acetoxy-1-cyclohexene-1-carboxylate Ethyl (1α,5α,6α)-5-acetoxy-7-oxabicyclo[4.1.0]hept-2-ene-3-carboxylate (91 mg, 0.40 mmol) obtained in Example 7 was dissolved in 3-pentanol (1.35 ml) and thereto was added boron trifluoride-diethyl ether complex (63 mg, 0.44 mmol) at room temperature. The mixture was stirred at room temperature for 1.5 hr and thereto was added saturated sodium hydrogen carbonate (5 ml). The reaction mixture was extracted with dichloromethane, washed with saturated brine and dried over anhydrous sodium sulfate. The solvent was distilled away and the residue was purified by silica gel column chromatography (ethyl acetate:hexane=1:4) to give the objective product (102 mg, 0.325 mmol, yield 81.2%).

IR(neat): 3508, 2966, 2937, 2878, 1718, 1657, 1464, 1369, 1236, 1082, 1037 cm$^{-1}$.

$^1$H-NMR(250 MHz): δ=6.77–6.75 (1H, m), 5.07–4.96 (1H, m), 4.21 (2H, q, J=7.2 Hz), 4.13–4.05 (1H, m), 3.83–3.75 (1H, m), 3.52–3.45 (1H, m), 3.01–2.90 (1H, m), 2.35–2.21 (1H, m), 2.12 (3H, s), 1.61–1.55 (4H, m), 1.31 (3H, t, J=7.2 Hz), 0.97–0.91 (6H, m).

EIMS m/z: 314(M$^+$), 272, 254, 227, 212, 185, 139, 111, 96.

HRMS calcd for C$_{16}$H$_{26}$O$_6$(M$^+$):314.1729, Found m/z= 314.1727.

Example 9

Synthesis of ethyl (3α,4β,5α)-3-(1-ethylpropoxy)-4-methanesulfonyloxy-5-acetoxy-1-cyclohexene-1-carboxylate Ethyl (3α,4β,5α)-3-(1-ethylpropoxy)-4-hydroxy-5-acetoxy-1-cyclohexene-1-carboxylate (11 mg, 0.034 mmol) obtained in Example 8 was dissolved in dichloromethane (0.1 ml), and thereto was added triethylamine (5 mg, 0.051 mmol). The mixture was stirred at room temperature for 5 min. The reaction mixture was cooled to 0° C. and thereto was added methanesulfonyl chloride (6 mg, 0.051 mmol). The mixture was stirred at room temperature for 1 hr. The reaction mixture was diluted with dichloromethane (20 ml) and the mixture was washed with saturated sodium hydrogen carbonate (20 ml) and saturated brine (10 ml), and dried over anhydrous sodium sulfate. The solvent was distilled away and the residue was purified by silica gel column chromatography (ethyl acetate:hexane=1:5) to give the objective product (13 mg, 0.033 mmol, yield 97.3%).

IR(neat): 2968, 2941, 2879, 1751, 1718, 1657, 1464, 1358, 1238, 1178, 1060 cm$^{-1}$.

$^1$H-NMR(250 MHz): δ=6.77–6.75 (1H, m), 5.21–5.11 (1H, m), 4.81–4.72 (1H, m), 4.34–4.28 (1H, m), 4.21(2H, q, J=7.2 Hz), 3.48–3.38 (1H, m), 3.08 (3H, s), 2.98–2.90 (1H, m), 2.50–2.38 (1H, m), 1.61–1.55 (4H, m), 1.31 (3H, t, J=7.2 Hz), 0.96–0.88 (6H, m).

EIMS m/z: 392(M$^+$), 363[(M-CH$_2$CH$_3$)$^+$], 305[(M-OC$_5$H$_{10}$)$^+$], 263, 245, 217, 199, 184, 173.

HRMS calcd for C$_{17}$H$_{28}$O$_8$S(M$^+$): 392.1505, Found m/z= 392.1508.

Example 10

Synthesis of ethyl (1β,5α,6β)-5-(1-ethylpropoxy)-7-oxabicyclo[4.1.0]hept-3-ene-3-carboxylate Ethyl (3α,4β,5α)-3-(1-ethylpropoxy)-4-methanesulfonyloxy-5-acetoxy-1-cyclohexene-1-carboxylate (34 mg, 0.086 mmol) obtained in Example 9 was dissolved in ethanol (3 ml), and potassium carbonate (60 mg, 0.043 mmol) was added at room temperature. The mixture was stirred at room temperature for 3 hr and saturated aqueous ammonium chloride solution (5 ml) was added. The mixture was extracted with dichloromethane. The organic layer was washed with saturated brine (5 ml), and dried over anhydrous sodium sulfate. The solvent was distilled away and the residue was purified by silica gel column chromotography (ethyl acetate:hexane=1:5) to give the objective product (21.7 mg, 0.085 mmol, yield 98.5%).

IR(neat): 1712, 1290, 1253, 1217, 1091, 1070, 1051 cm$^{-1}$.

$^1$H-NMR(250 MHz): δ=6.75–6.72 (1H, m), 4.39–4.37 (1H, m), 4.21 (2H, q, J=7.2 Hz), 3.51–3.45 (3H, m), 3.09–3.00 (1H, m), 2.45–2.36 (1H, m), 1.62–1.54 (4H, m), 1.31(3H, t, J=7.2 Hz), 1.01–0.93 (6H, m).

EIMS m/z: 236[(M-H$_2$O)$^+$], 225, 209, 191, 167, 151, 138, 121, 110.

HRMS calcd for C$_{14}$H$_{20}$O$_3$[(M-H$_2$O)$^+$]: 236.1413, Found m/z=236.1422.

INDUSTRIAL APPLICABILITY

According to the present invention, 5-oxy-7-oxabicyclo[4.1.0]hept-3-ene-3-carboxylic acid ester such as ethyl (1β,5α,6β)-5-(1-ethylpropoxy)-7-oxabicyclo[4.1.0]hept-3-ene-3-carboxylate useful as a synthetic intermediate for GS4104 being developed as an anti-influenza drug can be produced economically, industrially advantageously and efficiently in a large amount. The halolactone (I), which is a starting material in the method of the present invention, can be synthesized from an economical starting material. Therefore, according to the method of the present invention, 5-oxy-7-oxabicyclo[4.1.0]hept-3-ene-3-carboxylic acid ester can be produced from an economical starting material, without using an expensive starting material. The method of the present invention is suitable for producing 5-oxy-7-oxabicyclo[4.1.0]hept-3-ene-3-carboxylic acid ester industrially in a large amount.

This application is based on a patent application No. 11-371400 filed in Japan, the contents of which are hereby incorporated by reference.

What is claimed is:

1. A production method of a 5-oxy-7-oxabicyclo[4.1.0]hept-3-ene-3-carboxylic acid ester of the formula (X)

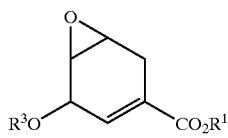
(X)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, which comprises:

reacting a 2-halogeno-7-oxabicyclo[2.2.1]heptane-5,3-carbolactone of the formula (I)

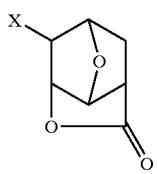
(I)

wherein X is a halogen atom, with a base, reacting the resulting compound with alkyl halide optionally having substituents, cycloalkyl halide optionally having substituents, alkenyl halide optionally having substituents, aryl halide optionally having substituents or aralkyl halide optionally having substituents, to give a 2,3-epoxy-7-oxabicyclo[2.2.1]heptane-5-carboxylic acid ester of the formula (III)

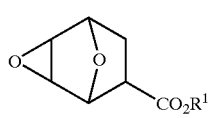
(III)

wherein $R^1$ is as defined above, reacting the obtained 2,3-epoxy-7-oxabicyclo[2.2.1]heptane-5-carboxylic acid ester with a base to give a 5-hydroxy-7-oxabicyclo[4.1.0]hept-2-ene-3-carboxylic acid ester of the formula (IV)

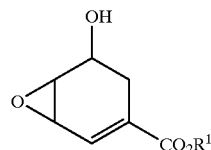
(IV)

wherein $R^1$ is as defined above, protecting a hydroxyl group of the obtained 5-hydroxy-7-oxabicyclo[4.1.0]hept-2-ene-3-carboxylic acid ester to give a 5-oxy-7-oxabicyclo[4.1.0]hept-2-ene-3-carboxylic acid ester of the formula (V)

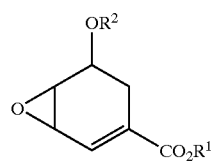
(V)

wherein $R^1$ is as defined above and $R^2$ is a hydroxyl-protecting group, reacting the obtained 5-oxy-7-oxabicyclo[4.1.0]hept-2-ene-3-carboxylic acid ester with an alcohol of the formula (VI)

$R^3OH$             (VI)

wherein $R^3$ is as defined above, in the presence of a Lewis acid to give a 4-hydroxy-3,5-dioxy-1-cyclohexene-1-carboxylic acid ester of the formula (VII)

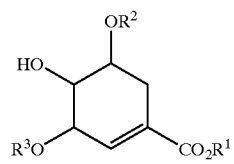
(VII)

wherein $R^1$, $R^2$ and $R^3$ are as defined above, reacting the obtained 4-hydroxy-3,5-dioxy-1-cyclohexene-1-carboxylic acid ester with a sulfonylating agent in the presence of a base to give a 3,5-dioxy-4-sulfonyloxy-1-cyclohexene-1-carboxylic acid ester of the formula (VIII)

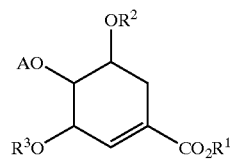
(VIII)

wherein $R^1$, $R^2$ and $R^3$ are as defined above and A is an organic sulfonyl group, removing the $R^2$ from the obtained 3,5-dioxy-4-sulfonyloxy-1-cyclohexene-1-carboxylic acid ester to give a 5-hydroxy-3-oxy-4-sulfonyloxy-1-cyclohexene-1-carboxylic acid ester of the formula (IX)

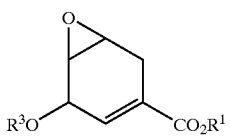

(IX)

wherein A, $R^1$ and $R^3$ are as defined above, and
reacting the obtained 5-hydroxy-3-oxy-4-sulfonyloxy-1-cyclohexene-1-carboxylic acid ester with a base.

2. A production method of a 5-oxy-7-oxabicyclo[4.1.0]hept-3-ene-3-carboxylic acid ester of the formula (X)

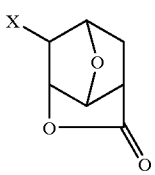

(X)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, which comprises:
reacting a 2-halogeno-7-oxabicyclo[2.2.1]heptane-5,3-carbolactone of the formula (I)

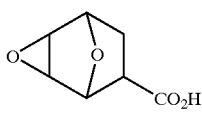

(I)

wherein X is a halogen atom, with a base to give a 2,3-epoxy-7-oxabicyclo[2.2.1]heptane-5-carboxylic acid of the formula (II)

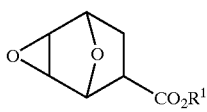

(II)

reacting the obtained 2,3-epoxy-7-oxabicyclo[2.2.1]heptane-5-carboxylic acid with an esterification agent to give a 2,3-epoxy-7-oxabicyclo[2.2.1]heptane-5-carboxylic acid ester of the formula (III)

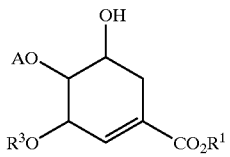

(III)

wherein $R^1$ is as defined above, reacting the obtained 2,3-epoxy-7-oxabicyclo[2.2.1]heptane-5-carboxylic acid ester with a base to give a 5-hydroxy-7-oxabicyclo[4.1.0]hept-2-ene-3-carboxylic acid ester of the formula (IV)

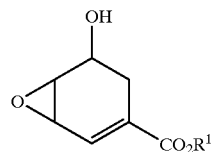

(IV)

wherein $R^1$ is as defined above,
protecting a hydroxyl group of the obtained 5-hydroxy-7-oxabicyclo[4.1.0]hept-2-ene-3-carboxylic acid ester to give a 5-oxy-7-oxabicyclo[4.1.0]hept-2-ene-3-carboxylic acid ester of the formula (V)

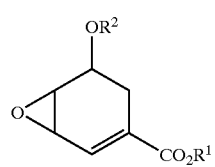

(V)

wherein $R^1$ is as defined above and $R^2$ is a hydroxyl-protecting group,
reacting the obtained 5-oxy-7-oxabicyclo[4.1.0]hept-2-ene-3-carboxylic acid ester with an alcohol of the formula (VI)

$R^3OH$ (VI)

wherein $R^3$ is as defined above, in the presence of a Lewis acid to give a 4-hydroxy-3,5-dioxy-1-cyclohexene-1-carboxylic acid ester of the formula (VII)

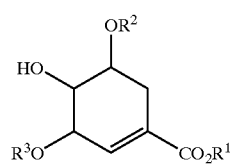

(VII)

wherein $R^1$, $R^2$ and $R^3$ are as defined above,
reacting the obtained 4-hydroxy-3,5-dioxy-1-cyclohexene-1-carboxylic acid ester with a sulfonylating agent in the presence of a base to give a 3,5-dioxy-4-sulfonyloxy-1-cyclohexene-1-carboxylic acid ester of the formula (VIII)

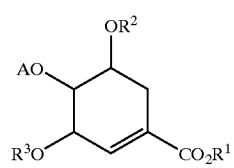

(VIII)

wherein $R^1$, $R^2$ and $R^3$ are as defined above and A is an organic sulfonyl group, removing the $R^2$ from the obtained 3,5-dioxy-4-sulfonyloxy-1-cyclohexene-1-carboxylic acid ester to give a 5-hydroxy-3-oxy-4-sulfonyloxy-1-cyclohexene-1-carboxylic acid ester of the formula (IX)

(IX)

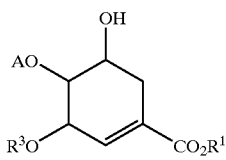

wherein A, $R^1$ and $R^3$ are as defined above, and reacting the obtained 5-hydroxy-3-oxy-4-sulfonyloxy-1-cyclohexene-1-carboxylic acid ester with a base.

3. A production method of a 2,3-epoxy-7-oxabicyclo[2.2.1]heptane-5-carboxylic acid of the formula (II)

(II)

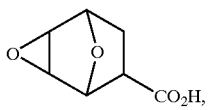

which comprises reacting a 2-halogeno-7-oxabicyclo[2.2.1]heptane-5,3-carbolactone of the formula (I)

(I)

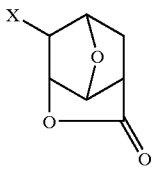

wherein X is a halogen atom, with a base.

4. A production method of a 2,3-epoxy-7-oxabicyclo[2.2.1]heptane-5-carboxylic acid ester of the formula (III-1)

(III-1)

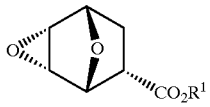

wherein $R^1$ is an alkyl group optionally having substituents, a cycloalkyl group optionally having substituents, an alkenyl group optionally having substituents, an aryl group optionally having substituents or an aralkyl group optionally having substituents, or the formula (III-2)

(III-2)

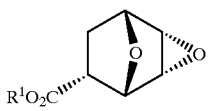

wherein $R^1$ is as defined above, which comprises reacting a 2,3-epoxy-7-oxabicyclo[2.2.1]heptane-5-carboxylic acid of the formula (II-1)

(II-1)

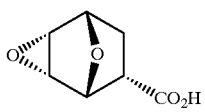

or the formula (II-2)

(II-2)

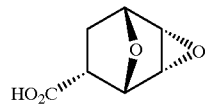

with an esterification agent.

5. A production method of a 2,3-epoxy-7-oxabicyclo[2.2.1]heptane-5-carboxylic acid ester of the formula (III)

(III)

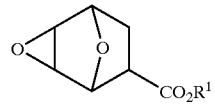

wherein $R^1$ is an alkyl group optionally having substituents, a cycloalkyl group optionally having substituents, an alkenyl group optionally having substituents, an aryl group optionally having substituents or an aralkyl group optionally having substituents, which comprises reacting a 2-halogeno-7-oxabicyclo[2.2.1]heptane-5,3-carbolactone of the formula (I)

(I)

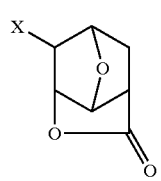

wherein X is a halogen atom, with a base, and reacting the resulting compound with alkyl halide optionally having substituents, cycloalkyl halide optionally having substituents, alkenyl halide optionally having substituents, aryl halide optionally having substituents or aralkyl halide optionally having substituents.

6. A production method of a 5-hydroxy-7-oxabicyclo[4.1.0]hept-2-ene-3-carboxylic acid ester of the formula (IV)

(IV)

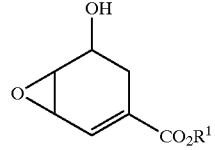

wherein $R^1$ is an alkyl group optionally having substituents, a cycloalkyl group optionally having substituents, an alkenyl group optionally having substituents, an aryl group optionally having substituents or an aralkyl group optionally having substituents, which comprises reacting a 2,3-epoxy-7-oxabicyclo[2.2.1]heptane-5-carboxylic acid ester of the formula (III)

(III)

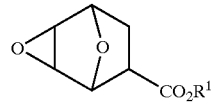

wherein $R^1$ is as defined above, with a base.

7. A production method of a 5-oxy-7-oxabicyclo[4.1.0]hept-3-ene-3-carboxylic acid ester of the formula (X)

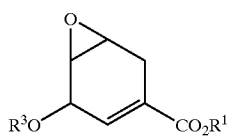
(X)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, which comprises:

reacting a 4-hydroxy-3,5-dioxy-1-cyclohexene-1-carboxylic acid ester of the formula (VII)

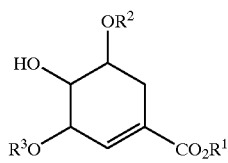
(VII)

wherein $R^1$ and $R^3$ are as defined above and $R^2$ is a hydroxyl-protecting group, with a sulfonylating agent in the presence of a base to give a 3,5-dioxy-4-sulfonyloxy-1-cyclohexene-1-carboxylic acid ester of the formula (VIII)

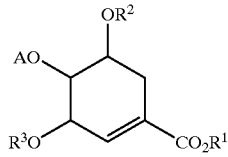
(VIII)

wherein $R^1$, $R^2$ and $R^3$ are as defined above and A is an organic sulfonyl group, removing the $R^2$ from the obtained 3,5-dioxy-4-sulfonyloxy-1-cyclohexene-1-carboxylic acid ester to give a 5-hydroxy-3-oxy4-sulfonyloxy-1-cyclohexene-1-carboxylic acid ester of the formula (IX)

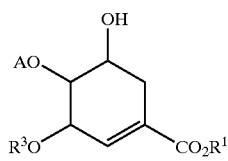
(IX)

wherein A, $R^1$ and $R^3$ are as defined above, and
reacting the obtained 5-hydroxy-3-oxy-4-sulfonyloxy-1-cyclohexene-1-carboxylic acid ester with a base.

8. A production method of a 5-oxy-7-oxabicyclo[4.1.0]hept-3-ene-3-carboxylic acid ester of the formula (X)

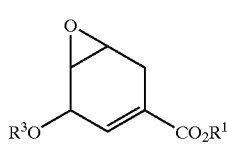
(X)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, which comprises:

removing the $R^2$ from a 3,5-dioxy-4-sulfonyloxy-1-cyclohexene-1-carboxylic acid ester of the formula (VIII)

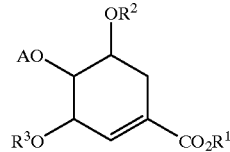
(VIII)

wherein $R^1$ and $R^3$ are as defined above, $R^2$ is a hydroxyl-protecting group and A is an organic sulfonyl group to give a 5-hydroxy-3-oxy-4-sulfonyloxy-1-cyclohexene-1-carboxylic acid ester of the formula (IX)

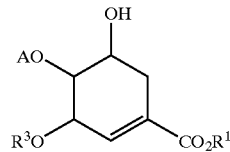
(IX)

wherein A, $R^1$ and $R^3$ are as defined above, and
reacting the obtained 5-hydroxy-3-oxy-4-sulfonyloxy-1-cyclohexene-1-carboxylic acid ester with a base.

9. A production method of a 5-oxy-7-oxabicyclo[4.1.0]hept-3-ene-3-carboxylic acid ester of the formula (X)

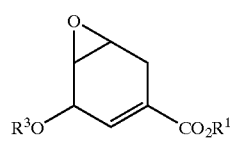
(X)

wherein $R^1$ and $R^3$ are independently an alkyl group optionally having substituents, a cycloalkyl group optionally having substituents, an alkenyl group optionally having substituents, an aryl group optionally having substituents or an aralkyl group optionally having substituents, which comprises reacting a 5-hydroxy-3-oxy-4-sulfonyloxy-1-cyclohexene-1-carboxylic acid ester of the formula (IX)

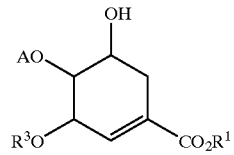
(IX)

wherein $R^1$ and $R^3$ are as defined above and A is an organic sulfonyl group, with a base.

10. An endo-2,3-epoxy-7-oxabicyclo[2.2.1]heptane-endo-5-carboxylic acid derivative of the formula (XI-1)

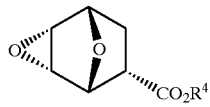

(XI-1)

wherein $R^4$ is a hydrogen atom, an alkyl group optionally having substituents, a cycloalkyl group optionally having substituents, an alkenyl group optionally having substituents, an aryl group optionally having substituents, an aralkyl group optionally having substituents or a metal capable of forming a carboxylic acid salt, or the formula (XI-2)

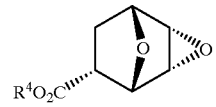

(XI-2)

wherein $R^4$ is as defined above.

* * * * *